United States Patent [19]

Forrester

[11] Patent Number: 5,393,495

[45] Date of Patent: Feb. 28, 1995

[54] METHOD AND APPARATUS FOR TESTING GASES, PARTICULARLY BREATH ALCOHOL

[75] Inventor: Glenn C. Forrester, Oakland, Calif.

[73] Assignee: Intoximeters, Inc., St. Louis, Mo.

[21] Appl. No.: 931,069

[22] Filed: Aug. 17, 1992

[51] Int. Cl.$^6$ ........................................... G01N 33/497
[52] U.S. Cl. ...................................... 422/83; 422/84
[58] Field of Search .................... 422/83, 84; 73/23.3, 73/23.21

[56] References Cited

U.S. PATENT DOCUMENTS 3,994,799  11/1976  Yao .
4,128,884  12/1978  England .
4,487,055  12/1984  Wolf .
4,770,026   9/1988  Wolf .
5,048,321   9/1991  Chow .

Primary Examiner—Timothy M. McMahon
Attorney, Agent, or Firm—Polster, Lieder, Woodruff & Lucchesi

[57] ABSTRACT

A method and apparatus for measuring the concentration of breath alcohol or other reactants is provided in which a breath sample is introduced to a fuel cell, wherein the number of electrons from the fuel cell resulting from oxidation of the alcohol in the breath rises to a peak and thereafter falls to a substantially steady minimum base to form a curve. The present method is based on the discovery that this curve, regardless of reactant concentration or age of fuel cell, is a log-normal distribution curve.

13 Claims, 3 Drawing Sheets

METHOD AND APPARATUS FOR TESTING GASES, PARTICULARLY BREATH ALCOHOL

BACKGROUND OF THE INVENTION

This invention relates to devices and methods for the quantitative determination of the concentration of a chemical constituent in a gaseous mixture. It has particular but not exclusive application to breath alcohol testing devices such as the ones sold by Intoximeters, Inc., 1901 Locust Street, St. Louis, Mo., under the trademark ALCO-SENSOR, and especially to such devices equipped with fuel cells constructed as described in Wolf U.S. Pat. Nos. 4,487,055 and 4,770,026, the disclosures of which are hereby incorporated by reference.

In breath alcohol testing devices presently used commercially, in which fuel cells are employed, the conventional way of determining breath alcohol is to measure a peak voltage across a resistor due to the flow of electrons obtained from the oxidation of breath alcohol on the surface of the fuel cell. There are a number of problems. The peaks become temporarily lower with repeated exposure to alcohol. The peaks also vary with temperature. In order to produce a high peak voltage, it is customary to put across the output terminals of the fuel cell a high external resistance, on the order of a thousand ohms, but the use of such a high resistance produces a voltage curve which goes to the peak and remains on a high plateau for an unacceptably long time. To overcome that problem, present systems provide for shorting the terminals, which drops the voltage to zero while the short is across the terminals. However, it is still necessary to let the cell recover, because if the short is removed in less than one-half to two minutes after the initial peak time, for example, the voltage creeps up. Peak values for the same concentration of alcohol decline with repeated use whether the terminals are shorted or not, and require 15–25 hours to recover to their original values.

Individual fuel cells differ in their characteristics. All of them slump with repeated exposure to alcohol in quick succession. Over time, their sensitivity decreases to a point at which they must be re-calibrated or replaced. Presently, the cell is replaced when it peaks too slowly, when it returns too slowly to a base line output, when the output at the peak declines beyond practical calibration, or when the background voltage begins creeping excessively after the short is removed from the cell terminals.

Wolf, U.S. Pat. No. 4,770,026, provides an apparatus and method that provides a measure of breath alcohol that is largely free of the drawbacks previously encountered with the use of fuel cells for this purpose. However, it remains dependent on the characteristic changes in a fuel cell's response curve caused by repeated exposure to alcohol and age. These changes increase the time required to perform an analysis and increase the time between successive analyses.

The present invention enhances the analytical capabilities of the device described in Wolf U.S. Pat. No. 4,770,026 by providing a new method for determining the level of breath alcohol or other gaseous constituent of a mixture. The improvement is applicable to a wide variety of other electronic analysis circuits associated with fuel cell detectors and to instruments for measuring a wide variety of reactive volatiles.

One of the objects of this invention is to reduce the time required for determining the level of breath alcohol or other reactive gases.

Another object is to reduce the computational requirements for such analysis.

Another object is to reduce the length of time required between successive such analyses.

Another object is to eliminate any error in a breath alcohol determination created by the residual effects of a previous test.

Other objects will become apparent to those skilled in the art in the light of the following description and accompanying drawing.

SUMMARY OF THE INVENTION

In accordance with one aspect of the present invention, generally stated, an improved method of measuring breath alcohol concentration is provided in which a breath sample is introduced to a fuel cell, wherein the number of electrons from the fuel cell resulting from oxidation of the alcohol in the breath rises to a peak and thereafter falls to a substantially steady minimum base to form a curve. The present invention provides a greatly simplified method for determining the area under the curve to a high degree of accuracy.

The present method is based on the discovery that this curve, regardless of reactant (e.g. alcohol, carbon monoxide, hydrogen, or other chemical compound for which the fuel cell is designed to react), concentration of reactant, or age of fuel cell, is a log-normal distribution curve. In the present method, the entire area under the curve is determined by identifying two points on the curve and calculating the parameters that define the entire curve as well as the entire area under that curve, thereby providing a measure of substantially all of the electrons generated by the oxidation (or reduction) of the alcohol or other reactant, and an intelligible signal representing that area is generated. The preferred method includes two additional steps: first, a step of establishing an absolute base line output of the cell (if any) and identifying points on the curve relative to that base line, and second, a step of establishing a secondary base line output immediately previous to introducing a sample to the fuel cell in order to determine the presence of residual effects from a previous test (if any), the value of which is used to mathematically determine a correction value for the subsequent test. The correction value is preferably based on the square of the secondary base line valued to take into account the area under the tail of the previous curve.

Apparatus in accordance with the present invention is provided for measuring a reactant in a gaseous sample by reacting the reactant in a fuel cell which produces a current that flows via output terminals through an external circuit. The current consists of those electrons generated at any point in time by the conversion of the substance to be analyzed, the current rising in response to the presence of the reactant in contact with the fuel cell and falling again to a base level to establish a current-time curve, the apparatus comprising means for calculating the parameters of the extrapolated log-normal curve, means for determining the area under the curve, means for adjusting for the residual effect of a previous test, and means for displaying a value indicating reactant concentration as a function of the area.

In the preferred apparatus of the present invention, an external resistor across the output terminals of the fuel cell has a resistance high enough to avoid bypassing significant current from the current amplifier, but low enough to maintain the stability of the cell between tests.

DESCRIPTION OF THE PREFERRED EMBODIMENT

Figure 1:
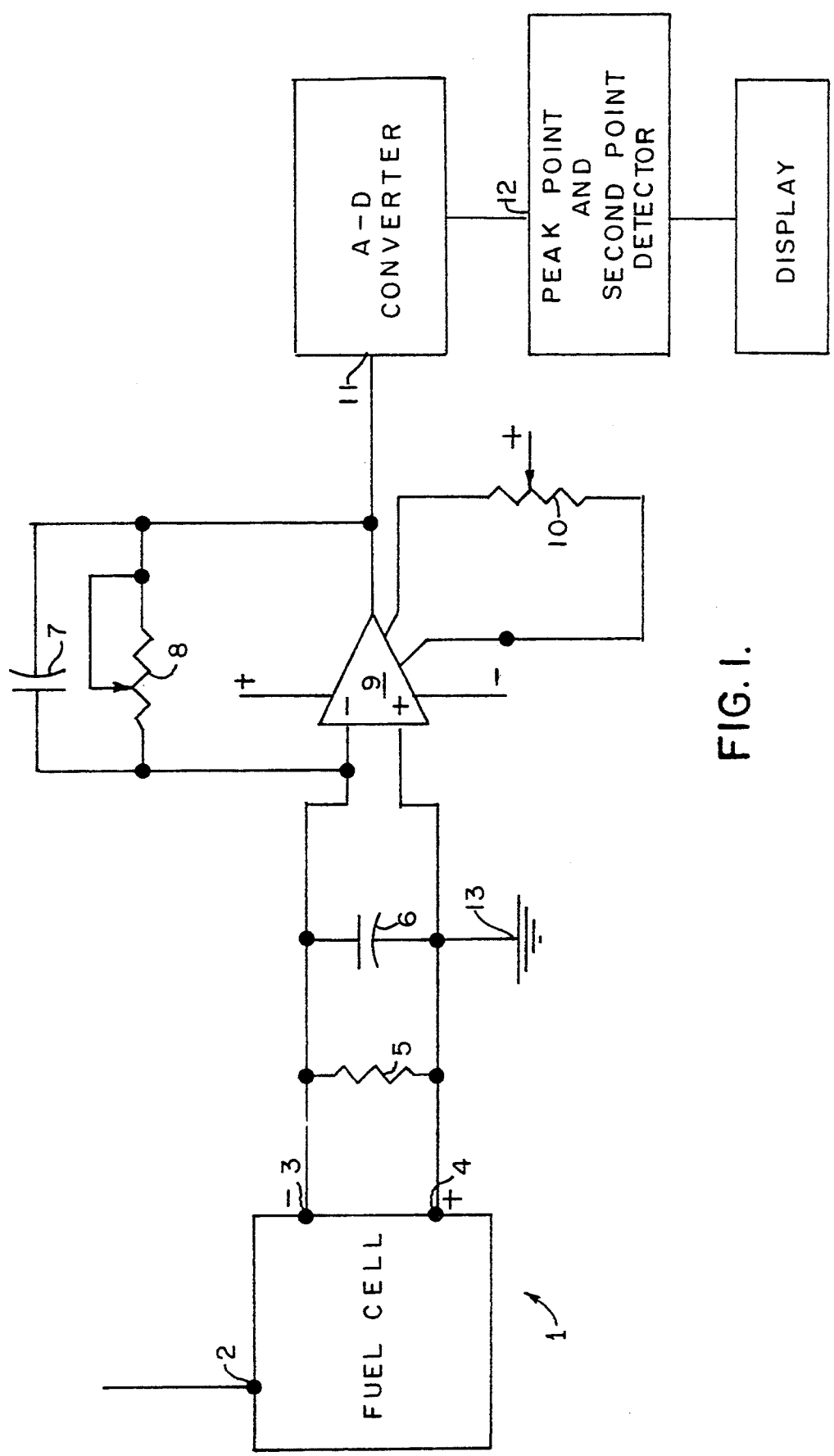
FIG. 1 is a circuit diagram showing one illustrative embodiment of circuit of this invention.
Figure 2:
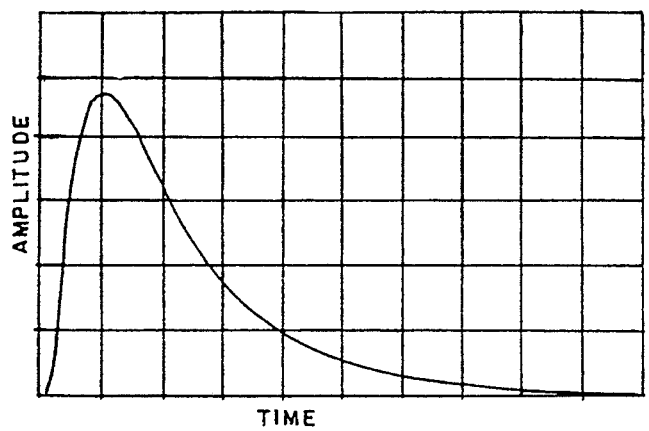
FIG. 2 is a graph showing the curve of current produced by the circuit of FIG. 1.
Figure 3:
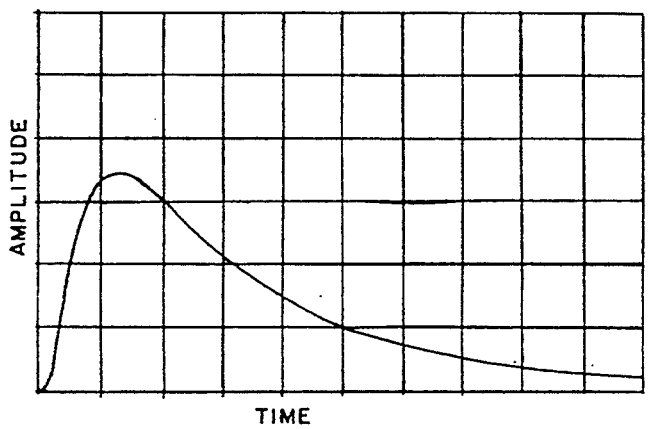
FIG. 3 is a graph showing the curve of current produced by a fuel cell which has been recently exposed to alcohol or has been in use for a long period of time.

Referring now to the drawings, and particularly to FIG. 1, for a circuit illustrating one embodiment of apparatus of this invention, reference numeral i indicates a fuel cell with terminals 2, 3 and 4. Terminals 3 and 4 are output terminals and terminal 2 is a biasing electrode which may or may not be included depending on the type of fuel cell configuration, in accordance with well-known practice. A resistor 5 is connected across the terminals 3 and 4. The resistor 5 illustratively has a resistance of 1.5 ohms. In practical usage, this value may vary widely, say from 1.5 ohms to 1000 ohms. A capacitor 6 is also connected across terminals 3 and 4. The capacitor 6, in this embodiment, has a capacitance of 0.1 µfd. Terminal 3 is connected to the negative input of an operational amplifier (op amp) 7. Terminal 4 is connected to a common or ground 13 as is the positive input of the op amp. In this embodiment, a 25k ohm potentiometer 8 provides feedback for gain control and a 2.2 µfd. capacitor 7 provides smoothing of the output. In this embodiment a potentiometer 10 connects to the offset terminals of the op amp providing zero offset for the op amp output. The output of the op amp 9 is electrically connected to the input of an analog to digital converter 11. The output of the analog to digital converter 11 is then electrically connected to a peak point and second point detector 12.

In the present invention, as in Wolf, U.S. Pat. No. 4,770,026, an output value is generated indicating percentage of breath alcohol. This value is a function of the total area under the curve (FIGS. 2-5) as generated by the method described herein. Unlike the Wolf, U.S. Pat. No. 4,770,026, the value is derived from treating the curve as a log-normal curve and determining only the peak point and a point on the tail of the curve.

In practicing the method of this invention on the device described, a fuel cell base line current is determined by measuring the output of the fuel cell circuit with no alcohol present. The device is then calibrated by using a standard, because every fuel cell is likely to have slightly different characteristics. The calculated area obtained must be divided by a factor so that the result displayed is the blood alcohol equivalent of the breath standard used. The various methods of calculating and applying this factor will be obvious to those skilled in the art. In the present example, the following formulas are utilized.

A common definition of the log-normal distribution curve is:

$$Y = a * \exp[-0.5*((ln(X/b))/c)^2]$$

where:
a = Amplitude
b = Center
c = Width

The formula for the area under this curve is:

$$Area = a*b*c*e^{(c^2/2)}*(2\pi)^{\frac{1}{2}}$$

The values of a and b are determined by using the device to measure the peak point on the curve. This is accomplished by regularly monitoring the output of the fuel cell and determining the maximum output of the fuel cell (adjusted for the fuel cell base line) (a) and the time from the beginning of analysis to the point at which the peak output occurred (b). The value of c can be derived from the values of a, b and the coordinates of another point on the curve. This point is chosen based on the desired speed of analysis and accuracy of analysis. By choosing a point at a later time (slower analysis) the accuracy of the area determination will be increased, and by choosing a point at an earlier time (faster analysis) the accuracy of the area determination will be decreased. The second point may be determined at a fixed time after the peak is detected, or it may be determined at a fixed value relative to the peak height, for example 0.66-0.06 times the peak height. The latter approach has the advantage that as the fuel cell ages, the accuracy of the device remains constant but the operator is warned to replace the cell when the analysis time becomes too long.

For any point on the curve after the peak point the value of c for the above area calculation can be derived from the formula:

$$c = (ln(u/b))/(-2*ln(v/a))^{\frac{1}{2}}$$

where
u = X(time), and
v = Y(amps − base line)

A secondary base line current ("test base line") is determined during the two or three seconds before the alcohol sample is taken into the fuel cell. This value is used to determine the existence of and level of residual activity from a previous test. A correction factor representative of the area under the tail of the curve from a previous test (or tests) is estimated by the following formula:

$$Correction\ factor = X^2/K$$

where:
X = the test base line current − the fuel cell base line current and
K = a constant value determined for a given fuel cell.

Figure 4:
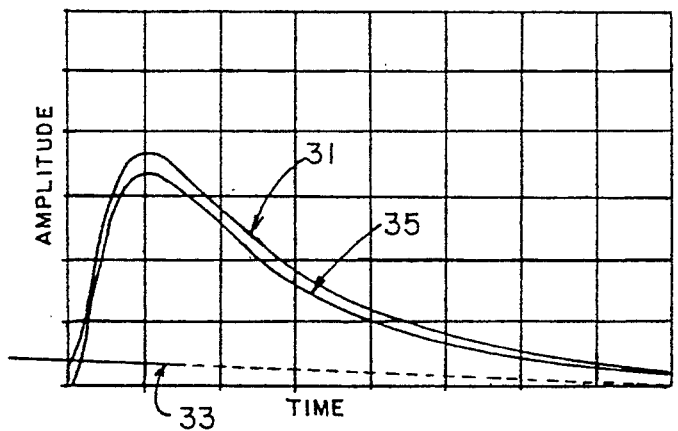
FIG. 4 is a graph showing the curve of current produced by a fuel cell which has not recovered completely from a recent exposure to alcohol, and further showing correction for the residual effects of the prior test in accordance with the present invention.
Figure 5:
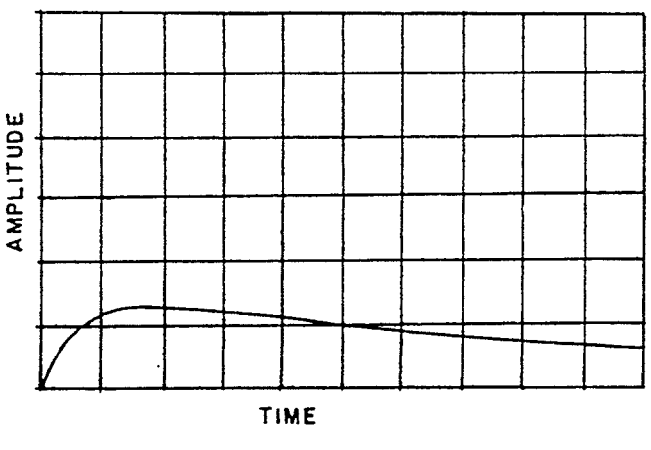
FIG. 5 is a graph showing the curve of current produced by a fuel cell which has either passed its practical useful lifetime in a commercial alcohol breath testing instrument or is attached to a high external resistance.
Figure 6:
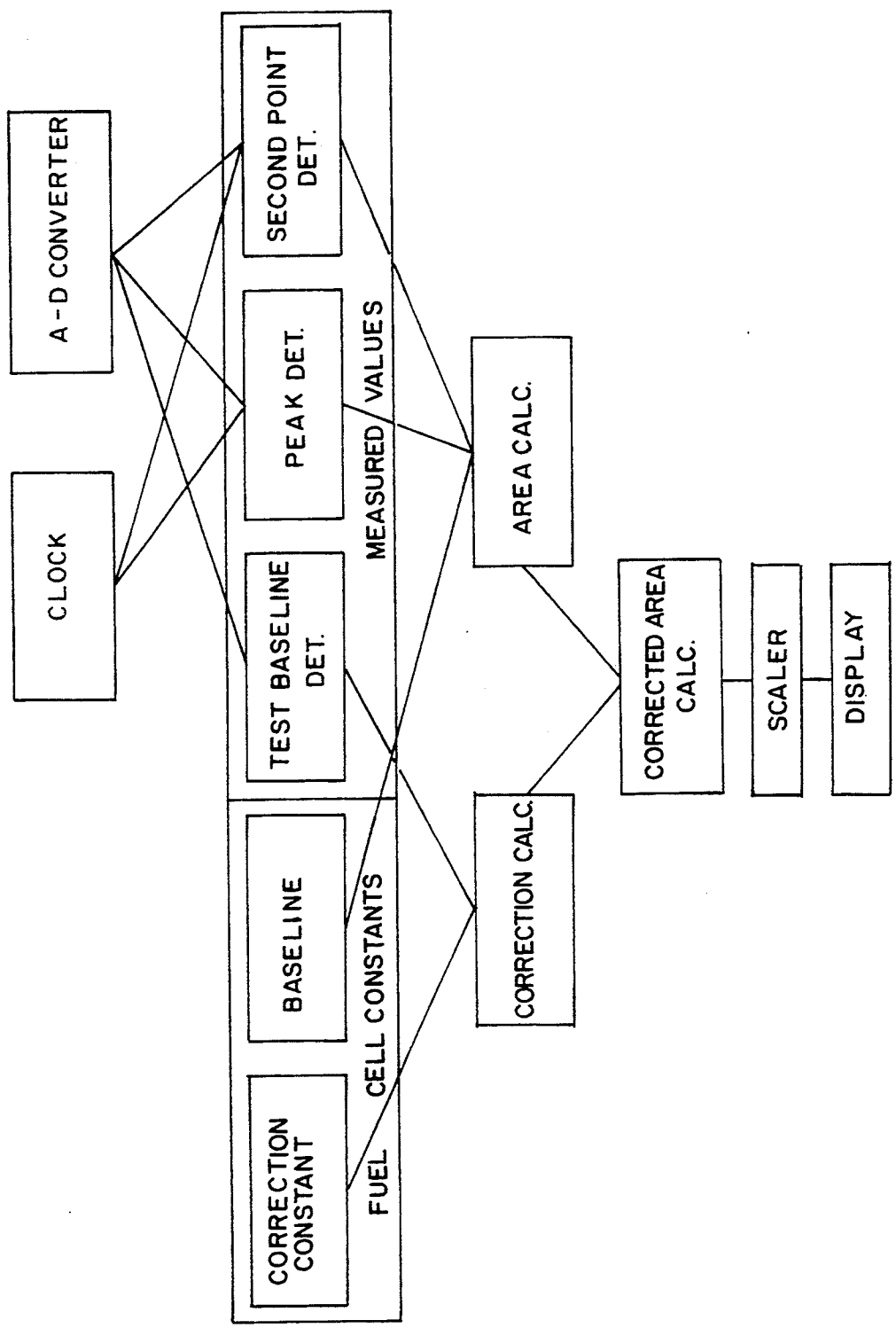
FIG. 6 is a logic diagram of a computer program for carrying out the preferred method.

As shown in FIG. 4, the area under the curve 31 is determined by the above method and the area attributable to a previous test, indicated by the area under line 33, is subtracted from the total area. The resulting area is indicated by the area under the curve 35.

It has been found by experimentation that the shape of the actual output curve of the fuel cell in a commercial breath analyzer differs slightly from a true log-normal curve. It is believed that this difference is caused by such factors as the finite time required for pulling the sample into the fuel cell chamber. Nonetheless, it has been found that the area under the actual curve differs by only about 0.1% from the area under a true log-normal curve. Therefore, the accuracy of the present method is believed to be well within the tolerances of most analytical uses.

It can be seen that, once calibrated, the device will give an accurate measure of the total alcohol content of the sample regardless of the initial height of the peak or the parameters of the curve. Accordingly, variations in peak height as a result of repeated use or degradation of the fuel cell or as a result of different temperatures will have no effect upon the accuracy of the alcohol determination. In practice, with degradation of the cell over time, the effect is to lengthen the time within which the measurement is to be taken. If a measurement time of ninety seconds, for example, is taken as the longest practical time limit in field use, then the cell can be used for a long time without being replaced. If there is any question of calibration, the device can be tested against an alcohol standard.

Numerous variations in the construction of the apparatus and the practice of the method of this invention, within the scope of the appended claims, will occur to those skilled in the art in the light of the foregoing disclosure. Merely by way of illustration and not of limitation, the resistance of the resistor between the fuel cell output terminals of the preferred device can be increased or decreased somewhat from the value shown but will always be low as compared with the conventional fuel cell breath analyzer, in which the external resistance between the terminals is between 300 and 1,000 ohms. The voltage output of the cell may be measured across the external resistor in a more conventional breath analyzer by connecting the positive terminal of the fuel cell to the non-inverting input of an operational amplifier. This configuration results in a somewhat slower response, since the electron flow is impeded by the resistor. Although the invention has been described as applied to a breath ethanol analyzer, and has particular utility in such a device, it may also be applied to other instruments which utilize a fuel cell to make quantitative determinations of a volatile, reactive constituent of a gas. Examples of such devices are breath analyzers which discriminate volatiles in the breath, such as the device described in Chow, U.S. Pat. No. 5,048,321 for discriminating alcohols; oxygen consumption analyzers; blood constituent analyzers such as described in Yao, U.S. Pat. No. 3,994,799; formaldehyde sensors; carbon monoxide sensors, and hydrogen sulfide sensors. When used in instruments designed to detect multiple reactants in a single sample, the reactants may be discriminated by the method of Chow, U.S. Pat. No. 5,048,321 or by known methods for discriminating populations having a log-normal distribution, such as the method described in England, U.S. Pat. No. 4,128,884. These variations are merely illustrative.

I claim:

1. In the method of measuring the concentration of a reactant in a gaseous sample in which the sample is introduced to a fuel cell, the reactant is reacted at the fuel cell, and an electrical output from the fuel cell resulting from reaction of the reactant is measured, the output rising to a peak and thereafter falling to a substantially steady minimum base to form a curve, the improvement comprising fitting the electrical output to a log-normal curve, said method including a step of determining said peak of said curve, a step of determining a point on said curve between said peak and said minimum, and a step of calculating the entire area under the curve from the identification of said peak and said point.

2. The method of claim 1 including a step of establishing a fuel cell base line output of said cell at least once before samples are introduced to the fuel cell, thereafter a step of establishing a test base line before reaction of said reactant begins, and a step of calculating a correction factor from the fuel cell base line and the test base line, the correction factor representing the residual effect of a previous test.

3. The method of claim 2 including a step of making an initial area calculation relative to the fuel cell base line and subtracting the calculated correction factor.

4. The method of claim 1 wherein the period between the step of determining said peak of said curve and the step of determining a point on said curve between said peak and said minimum is less than on the order of fifteen times the length of time between the beginning of said reaction and the reaching of a peak output.

5. The method of claim 4 wherein the period between the step of determining said peak of said curve and the step of determining a point on said curve between said peak and said minimum is less than on the order of eight times the length of time between the beginning of said reaction and the reaching of a peak output.

6. The method of claim 1 wherein the reaction is an oxidation of the reactant.

7. The method of claim 1 wherein the reactant is ethanol, the method including a step of introducing a breath sample to the fuel cell.

8. The method of claim 1 further including a step of generating a signal representing concentration of said reactant as a function of said area.

9. The method of claim 1 wherein said output is an electric current.

10. An apparatus for measuring a reactant in a gaseous sample by reacting the reactant in a fuel cell which produces an electrical signal, said signal rising in response to the presence of said reactant in contact with said fuel cell and falling again to a base level to establish a signal-time curve, the apparatus further comprising means for determining a peak of said curve, means for determining a second point on the curve, and means for extrapolating the area under the curve as a log-normal curve based on said peak and said second point.

11. The apparatus of claim 10 further comprising means for adjusting the area under the curve for the residual effect of a previous test.

12. The apparatus of claim 11 wherein the means for adjusting the area under the curve comprise means for storing a test base line before reaction of said reactant begins, and means for calculating a correction factor from the fuel cell base line.

13. The apparatus of claim 10 wherein the reactant is alcohol, the apparatus including means for introducing a breath sample to said fuel cell.

* * * * *